United States Patent
Birring et al.

(10) Patent No.: US 7,883,497 B2
(45) Date of Patent: Feb. 8, 2011

(54) ABSORBENT ARTICLE INCLUDING AN ABSORBENT STRUCTURE

(75) Inventors: Mats Birring, Göteborg (SE); Kent Vartiainen, Lerum (SE); Eje Österdahl, Västra Frölunda (SE); Göran Forsbring, Kungsbacka (SE); Berith Porsö, Partille (SE); Charlotta Hansson, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 164 days.

(21) Appl. No.: 10/788,202

(22) Filed: Feb. 27, 2004

(65) Prior Publication Data

US 2005/0192550 A1 Sep. 1, 2005

Related U.S. Application Data

(60) Provisional application No. 60/450,330, filed on Feb. 28, 2003.

(51) Int. Cl.
*A61F 13/532* (2006.01)
*A61F 13/534* (2006.01)

(52) U.S. Cl. .................. 604/385.01; 604/365; 604/378

(58) Field of Classification Search ......... 604/378–380, 604/385.17, 385.21, 385.101, 385.19
See application file for complete search history.

(56) References Cited

U.S. PATENT DOCUMENTS

| | | | | |
|---|---|---|---|---|
| 3,375,827 A | * | 4/1968 | Bletzinger et al. | 604/380 |
| 3,525,337 A | * | 8/1970 | Simons et al. | 604/366 |
| 3,699,966 A | * | 10/1972 | Chapuis | 604/377 |
| 3,736,931 A | * | 6/1973 | Glassman | 604/385.19 |
| 3,901,238 A | * | 8/1975 | Gellert et al. | 604/366 |
| 3,924,627 A | | 12/1975 | Nystrand | |
| 4,413,996 A | | 11/1983 | Taylor | |
| 4,576,596 A | * | 3/1986 | Jackson et al. | 604/370 |

(Continued)

FOREIGN PATENT DOCUMENTS

EP 0 558 070 1/1993

(Continued)

OTHER PUBLICATIONS

Written Opinion and International Preliminary Report PCT/SE2004/000258.*

(Continued)

*Primary Examiner*—Karin M Reichle
(74) *Attorney, Agent, or Firm*—Buchanan Ingersoll & Rooney PC

(57) ABSTRACT

An absorbent article includes an absorbent structure. The edge portions in the absorbent structure's middle portion have a first mean pore size, and the central portion in the middle portion of the absorbent structure has a second mean pore size, the first mean pore size being greater than the second mean pore size. The absorbent article can be folded along the longitudinal centre axis so that a part of the article on one side of the longitudinal centre line and a corresponding part of the article on the other side of the longitudinal centre line are brought together to lie against one another at a plane of the longitudinal centre line on the upper surface of the article. The edge portions which have the greater, first mean pore size thereby form an area of the absorbent article that is first wetted during use.

17 Claims, 8 Drawing Sheets

U.S. PATENT DOCUMENTS

| | | | | |
|---|---|---|---|---|
| 4,578,070 | A * | 3/1986 | Holtman | 604/378 |
| 4,685,914 | A * | 8/1987 | Holtman | 604/368 |
| 4,795,453 | A * | 1/1989 | Wolfe | 604/385.101 |
| 4,874,457 | A * | 10/1989 | Swieringa | 156/474 |
| 4,946,454 | A | 8/1990 | Schmidt | |
| 4,988,344 | A * | 1/1991 | Reising et al. | 604/368 |
| 5,197,959 | A * | 3/1993 | Buell | 604/385.23 |
| 5,312,386 | A * | 5/1994 | Correa et al. | 604/379 |
| 5,324,278 | A * | 6/1994 | Visscher et al. | 604/385.04 |
| 5,330,457 | A * | 7/1994 | Cohen | 604/378 |
| 5,460,621 | A * | 10/1995 | Gertzman et al. | 604/358 |
| 5,460,623 | A | 10/1995 | Emenaker et al. | |
| 5,505,719 | A * | 4/1996 | Cohen et al. | 604/372 |
| 5,509,915 | A * | 4/1996 | Hanson et al. | 604/378 |
| 5,591,149 | A * | 1/1997 | Cree et al. | 604/378 |
| 5,609,588 | A * | 3/1997 | DiPalma et al. | 604/369 |
| 5,611,879 | A * | 3/1997 | Morman | 156/201 |
| 5,653,842 | A | 8/1997 | Kuen | |
| 5,683,374 | A * | 11/1997 | Yamamoto et al. | 604/385.29 |
| 5,968,027 | A * | 10/1999 | Cole et al. | 604/385.01 |
| 6,198,019 | B1 * | 3/2001 | Hansson et al. | 604/378 |
| 6,254,584 | B1 * | 7/2001 | Osborn et al. | 604/385.17 |
| 6,261,277 | B1 * | 7/2001 | Osborn et al. | 604/385.17 |
| 6,441,268 | B1 | 8/2002 | Edwardsson | |
| 6,734,335 | B1 * | 5/2004 | Graef et al. | 604/365 |
| 6,974,891 | B2 * | 12/2005 | Wallstrom | 604/379 |
| 2003/0060791 | A1 * | 3/2003 | Drevik | 604/380 |
| 2004/0087928 | A1 * | 5/2004 | Ducker | 604/385.01 |
| 2008/0132136 | A1 * | 6/2008 | Uematsu et al. | 442/414 |

FOREIGN PATENT DOCUMENTS

| | | |
|---|---|---|
| EP | 0 254 476 A2 | 1/1998 |
| ES | 2175499 | 11/2002 |
| GB | 2 082 643 A | 3/1982 |
| JP | 6-39000 | 2/1994 |
| JP | 9-507136 | 7/1997 |
| JP | 2003-501212 | 1/2003 |
| WO | WO 95/17870 | 7/1995 |
| WO | WO 00/76445 | 12/2000 |

OTHER PUBLICATIONS definition of "wrap", Merriam Webster OnLine.*

Translation of Japanese Notice of Reasons for Rejection issued Dec. 8, 2009 in corresponding JP 2006-502815.

Translation of Columbian Official Action issued Feb. 8, 2009 in corresponding CO 05083253.

* cited by examiner

ABSORBENT ARTICLE INCLUDING AN ABSORBENT STRUCTURE

This application claims the benefit under 35 U.S.C. §119 of U.S. Provisional Application No. 60/450,330 entitled "Absorbent Article Including An Absorbent Structure" and filed on Feb. 28, 2003, the entire content of which is hereby incorporated by reference.

TECHNICAL FIELD

The present invention relates to an absorbent article such as a diaper, an incontinence protector, a sanitary towel or the like, having a transverse direction, a longitudinal direction and a centre axis extending in the longitudinal direction, and a direction of thickness, the article comprising a liquid-permeable cover sheet arranged on an upper surface of the article, a backing sheet arranged on a lower surface of the article, and an absorbent structure enclosed between these sheets, the absorbent structure having, in the longitudinal direction, a middle portion and two opposite end portions and having, in the transverse direction, a central portion and two opposite edge portions.

BACKGROUND ART

An absorbent structure for absorbent articles, such as diapers, incontinence protectors and sanitary towels which are intended to be used once and disposed of, is usually made up of one or more sheets of hydrophilic fibres, for example cellulose fluff pulp. Superabsorbents are also often included, which are polymers with an ability to absorb many times their own weight of water or body fluid. In addition, the absorbent structure can also contain further components, for example in order to improve its liquid-spreading properties or to increase its stability and its ability to withstand deformation during use.

An important problem encountered primarily in the case of diapers and incontinence protectors for adults, intended to receive and absorb relatively large amounts of fluid, is that these often leak before their total absorption capacity has been fully utilized. Since, when urinating, large amounts of fluid are often released in the space of a few seconds, this can lead to the absorbent structure being locally saturated with liquid in the liquid-receiving zone, i.e. the liquid does not have time to spread to other parts of the absorbent structure. This means that additional liquid released by the user leaks out of the diaper. This kind of early leakage is of course a source of considerable irritation both for the user and for the person caring for the user. The leakage problem is accentuated upon repeated wetting.

EP 254,476 describes an absorbent structure which, in a zone substantially in front of the wetting area, has a lower weight per unit area and a lower density compared to surrounding portions of the absorbent structure. In this way, a high liquid absorption capacity in the wetting area is achieved, after which the liquid can spread out farther and is stored in the surrounding areas of the absorbent structure.

GB 2,082,643 further describes an absorbent structure with a substantially uniform weight per unit area, but with a density gradient in the longitudinal direction, such that the density increases towards the end portions of the absorbent structure.

U.S. Pat. No. 4,413,996 describes an absorbent structure for diapers which has a liquid-collecting recess or well in the wetting area. A porous wadding can be arranged, if appropriate, in this well.

However, there is still room for improvement as regards the liquid absorption capacity and the spreading ability, in particular in the case of products which are intended to take up large amounts of liquid in a short period of time.

SUMMARY OF THE INVENTION

With the present invention, an absorbent article, such as a diaper, incontinence protector, or sanitary towel which is intended to be used once and disposed of, has been obtained which substantially eliminates the problems which have been associated with previously known articles of this kind.

An absorbent article according to the invention is characterized principally in that the edge portions in the absorbent structure's middle portion, within at least part of the direction of thickness, have a first mean pore size, and in that the central portion in the absorbent structure's middle portion has a second mean pore size within at least part of the direction of thickness, the first mean pore size being greater than the second mean pore size, and in that the absorbent article can be folded along the longitudinal centre axis (II-II) (also referred to as the longitudinal centre line or centre line throughout this disclosure) so that a part of the article, on one side of the centre line (II-II) extending in the longitudinal direction, is brought to lie against a corresponding part of the article on the other side of the centre line (II-II) extending in the longitudinal direction on the upper surface of the article, and the portions which have the greater, first mean pore size constitute a liquid-receiving zone when the article is in use. That is, at least a part of the article on one side of the longitudinal centre line II-II and the corresponding part of the article on the other side of the longitudinal centre line II-II are brought together to lie against one another at a plane of the longitudinal centre line II-II. The criterion that the first mean pore size is greater than the second mean pore size applies at least in the dry state, but the first mean pore size is preferably greater than the second mean pore size both in the dry state and in the wet state. Having a difference in mean pore size permits draining of liquid from the liquid-receiving zone to the areas with the second, lesser mean pore size.

With the present invention, an absorbent article is obtained which is intended to be used in a folded state. Folded state means that the article is folded along its longitudinal centre axis, at least in the middle portion of the article, so that parts of the article on each side of the longitudinal centre axis are folded towards one another. The advantage of such an article is that in the folded state it can take up a large amount of liquid in a short space of time, which substantially reduces the risk of the absorbent structure becoming locally saturated with liquid in the liquid-receiving zone, which in turn reduces the risk of leakage. Another advantage of an article according to the invention is that the article when in use, i.e. in the folded state, has a narrow crotch area. The narrow crotch area creates a good fit and means that the risk of the article chafing against the user's thighs during use is reduced. By virtue of the fact that the article is folded when in use, it is also possible to design an article which, before folding, is wider than a conventional diaper. This means that the total absorption capacity in the crotch area of the article can be very high.

According to one embodiment of the invention, the absorbent article has a transverse direction, a longitudinal direction, a longitudinal centre axis extending in the longitudinal direction, and a direction of thickness. The article has a liquid-permeable cover sheet arranged on an upper surface of the article, a backing sheet arranged on a lower surface of the article, and an absorbent structure enclosed between the liquid-permeable cover sheet and the backing sheet, the absorbent structure having a transverse direction, a longitudinal direction, a longitudinal centre axis extending in the longitudinal direction, and a direction of thickness and having a sheet. The sheet has a substantially uniform thickness prior to use and defines, in the longitudinal direction, a middle portion and two opposite end portions and, in the transverse direction, a central portion and two opposite edge portions. The edge portions in the middle portion of the sheet have a first mean pore size, and the central portion in the middle portion of the sheet has a second mean pore size; the first mean pore size being greater than the second mean pore size. The edge portions in the middle portion of the sheet have the first mean pore size throughout the entire direction of thickness of the sheet at the time the absorbent structure is folded. The central portion in the middle portion of the sheet has the second mean pore size throughout the entire direction of thickness of the sheet at the time the absorbent structure is folded. The absorbent structure is folded transversely in half along the longitudinal centre axis of the absorbent structure at least along the middle portion of the sheet, an upper face of the edge portion in the middle portion of the sheet on one side of the longitudinal centre axis of the absorbent structure and a corresponding upper face of the edge portion in the middle portion of the sheet on the other side of the longitudinal centre axis of the absorbent structure being brought together to lie against one another at a plane of the longitudinal centre axis on an upper surface of the absorbent structure. The edge portions of the sheet which have the greater, first mean pore size form an area of the absorbent structure that during use receives liquid first before other areas of the absorbent structure and thus constitutes a liquid-receiving zone.

According to one embodiment, the liquid-permeable cover sheet, on one side of the longitudinal centre axis (II-II), is connected to the liquid-permeable cover sheet on the other side of the longitudinal centre axis (II-II). The cover sheet can, for example, be connected by adhesive bonding or by thermal welding. The connection is preferably intermittent, for example at two or more points. The advantage of this design is that the article is permanently in a correctly folded state and the risk of the article being wrongly folded or of its unfolding during use is eliminated.

According to one embodiment, the absorbent structure has an upper surface directed towards the liquid-permeable cover sheet and a lower surface directed towards the backing sheet, the absorbent structure being folded along the longitudinal centre axis (II-II) so that at least a part of the upper surface on one side of the longitudinal centre axis (II-II) in the middle portion of the absorbent structure lies against a part of the upper surface on the other side of the longitudinal centre axis (II-II). That is, at least a part of the upper surface on one side of the longitudinal centre line II-II and the corresponding part of the upper surface on the other side of the longitudinal centre line II-II are brought together to lie against one another at a plane of the longitudinal centre line II-II.

An absorbent structure according to one embodiment of the invention has a transverse direction, a longitudinal direction, a longitudinal centre axis extending in the longitudinal direction, and a direction of thickness. The absorbent structure has sheet having a substantially uniform thickness prior to use, the sheet defining a middle portion and two opposite end portions in the longitudinal direction, and, in the transverse direction, a central portion and two opposite edge portions. The edge portions in the middle portion of the sheet have a first mean pore size, and the central portion in the middle portion of the sheet has a second mean pore size; the first mean pore size being greater than the second mean pore size. The edge portions in the middle portion of the sheet have the first mean pore size throughout the entire direction of thickness of the sheet at the time the absorbent structure is folded. The central portion in the middle portion of the sheet has the second mean pore size throughout the entire direction of thickness of the sheet at the time the absorbent structure is folded. The absorbent structure is folded transversely in half along the longitudinal centre axis at least along the middle portion of the absorbent structure, wherein an upper face of the edge portion in the middle portion of the sheet on one side of the longitudinal centre axis and a corresponding upper face of the edge portion in the middle portion of the sheet on the other side of the longitudinal centre axis are brought together to lie against one another at a plane of the longitudinal centre axis on an upper surface of the absorbent structure. The edge portions of the sheet which have the greater, first mean pore size form an area of the absorbent structure that during use receives liquid first before other areas of the absorbent structure and thus constitutes a liquid-receiving zone.

To ensure that, in the folded state, the bearing of the upper surface on each side of the longitudinal centre axis in the middle portion of the absorbent structure is permanent, in one embodiment the upper surface on one side of the longitudinal centre axis in the middle portion of the absorbent structure is connected to the upper surface on the other side of the longitudinal centre axis. The connection can be obtained, for example, by adhesive bonding or by thermal welding. The advantage of such an embodiment is that the absorbent structure is permanently in a folded state and the risk of the absorbent structure unfolding is eliminated.

According to one embodiment, the edge portions in the middle portion of the absorbent structure have the first mean pore size throughout the entire thickness of the absorbent structure. This means that the liquid-receiving zone, i.e. the area with material having the greater pore size, covers the whole crotch portion in that part of the absorbent structure that is directed towards the user. By virtue of the fact that the article is folded when in use, the absorbent structure can be wider than an absorbent structure in an unfolded diaper. This means that both the liquid-receiving capacity and the storing capacity of an absorbent structure according to this embodiment is very high.

According to another embodiment, the edge portions of the end portions in the absorbent structure also have the first mean pore size, within at least part of the direction of thickness. The advantage of this embodiment is that the liquid-receiving zone in the longitudinal direction of the article is longer. A further advantage of such an embodiment is that such an absorbent structure is easier to produce.

In the direction of thickness, the absorbent structure can be made up of a first sheet and a second sheet. The first sheet can have a smaller extent in the longitudinal direction than the second sheet.

According to a preferred embodiment, the absorbent structure has a first mean pore size which is at least 1.1 times as great as the second mean pore size.

According to yet another embodiment, the absorbent structure has a first mean pore size which is at least 1.3 times as great as the second mean pore size.

According to one embodiment, the liquid-receiving zone has a lower density than the area comprising the second, lesser mean pore size. For example, the liquid-receiving zone has a density of between 0.02 and 0.2 $g/cm^3$, and the density is preferably between 0.06 and 0.15 $g/cm^3$. In such a structure, the area having the second, lesser mean pore size has a density of between 0.1 and 1.0 $g/cm^3$, preferably between 0.12 and 0.6 $g/cm^3$.

DETAILED DESCRIPTION OF THE FIGURES

Figure 1:
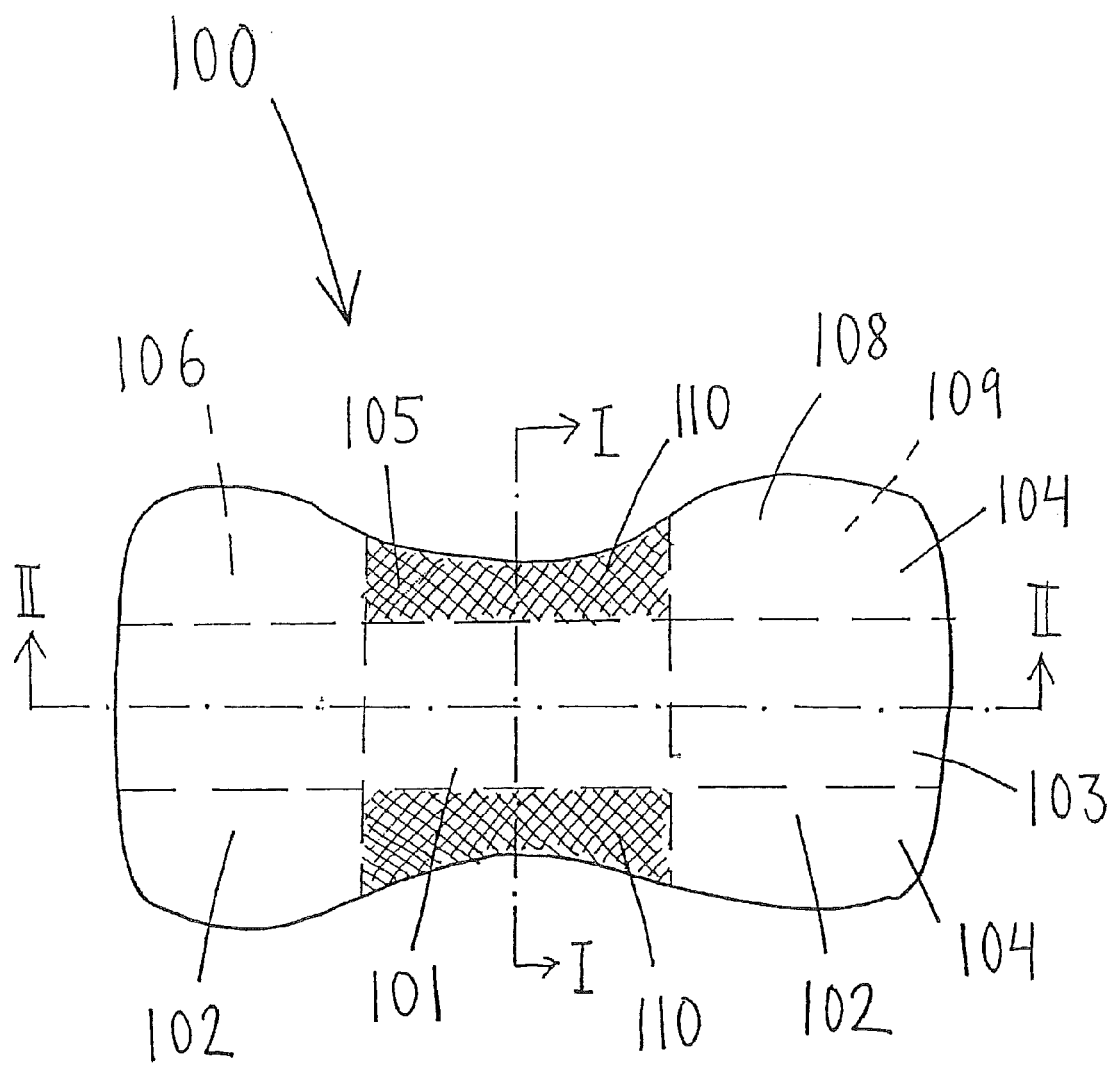
FIG. 1 shows a plan view of an absorbent structure according to the invention.
Figure 7:
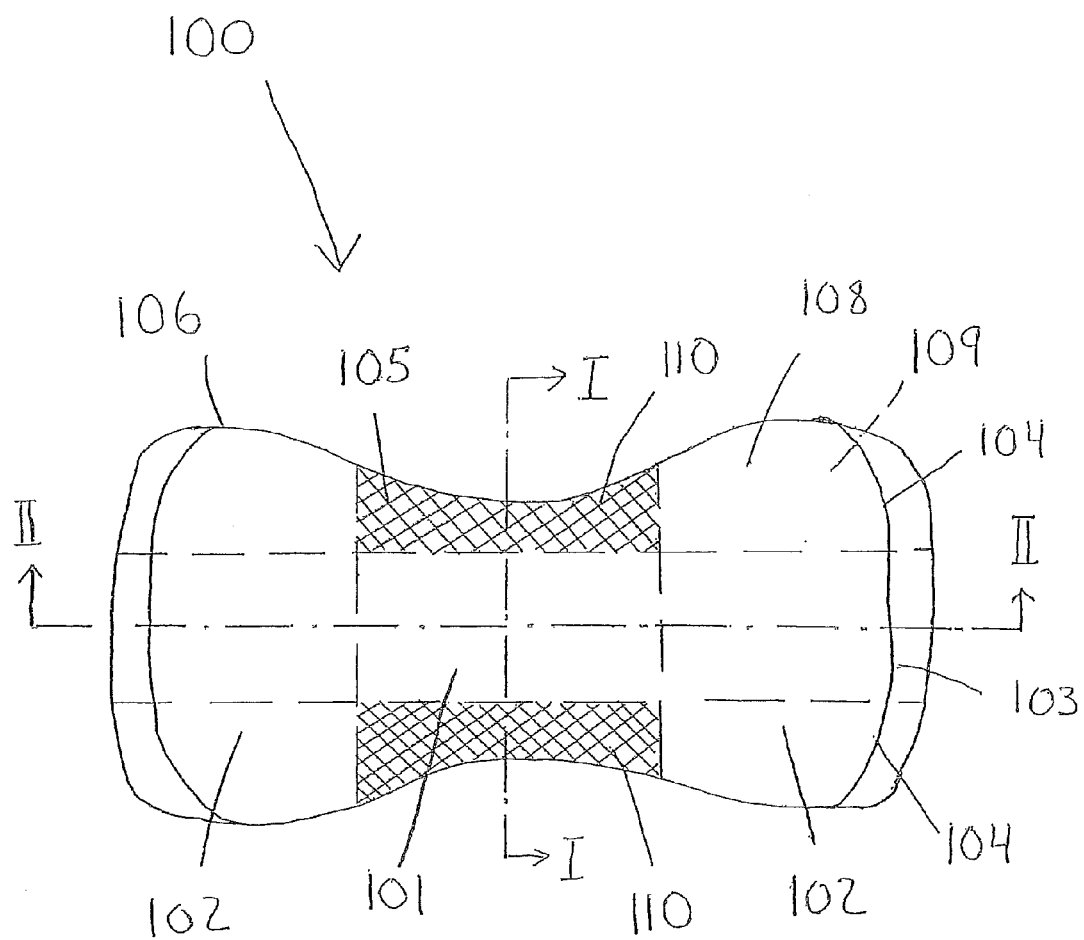
FIG. 7 shows a plan view of an alternative embodiment of an absorbent structure according to the invention.

FIG. 1 shows a plan view of an absorbent structure 100 according to the invention. The absorbent structure 100 shown in FIG. 1 has, in its plane, a transverse direction which in FIG. 1 is shown by a transverse centre line I-I, and a longitudinal direction which in FIG. 1 is shown by a longitudinal centre line II-II. FIG. 1 also shows a direction of thickness at right angles to the plane. In the plane of the absorbent structure 100, it has an upper face 108 and an opposite lower face 109. In the longitudinal direction, the absorbent structure 100 has a middle portion 101, and two opposite end portions 102. In the transverse direction, the absorbent structure 100 has a central portion 103 and two edge portions 104 on opposite sides of the central portion 103. In the direction of thickness, the absorbent structure further comprises a first sheet 105 and a second sheet 106. The first sheet 105 can have a smaller extent in the longitudinal direction than the second sheet 106, as shown in FIG. 7. The first sheet 105 is the sheet of the absorbent structure which, during use in an absorbent article, is intended to be nearest to the user. The first sheet 105 has areas with different mean pore sizes. In the middle portion 101 of the absorbent structure 100, the edge portions 104 of the absorbent structure have a first mean pore size and, in the middle portion 101 of the absorbent structure, the central portion 103 has a second mean pore size. The two end portions 102 of the first sheet 105 also have the second mean pore size. The first mean pore size is greater than the second mean pore size. When the absorbent structure is used in an absorbent article, the absorbent structure 100 is intended to be folded along its longitudinal centre line II-II such that at least the upper face 108 on one side of the longitudinal centre line II-II in the middle portion 101 lies against the upper face on the other, opposite side of the longitudinal centre line II-II in the middle portion 101 of the absorbent structure, and the portions which have the greater, first mean pore size constitute a liquid-receiving zone 110. That is, at least the upper face 108 on one side of the longitudinal centre line II-II and the corresponding upper face on the other, opposite side of the longitudinal centre line II-II are brought together to lie against one another at a plane of the longitudinal centre line II-II.

During use of the absorbent article, the edge portions 104 of the absorbent structure in the middle portion 101 constitute the part of the absorbent structure that is placed in the area in the absorbent structure 100 which is first wetted, namely the liquid-receiving zone 110.

The fibre material in the liquid-receiving zone 110 comprises, for example, synthetic fibres, such as polyethylene, polypropylene, polyester or copolymers thereof. It is also possible for the synthetic fibres to be two-component fibres. Another example of fibre material in the liquid-receiving zone is cellulose fibres of mechanical pulp, thermomechanical pulp or chemi-thermomechanical pulp (CTMP). These pulps have relatively coarse fibres with residual lignin, as a result of which they have a relatively large pore volume and high wetting resilience and are comparatively easy to drain of liquid. A high wetting resilience means that the fluff pulp substantially retains its structure even after wetting. Other fluff pulps too with similar properties can be used, for example chemically stiffened cellulose fibres. Another example of a suitable material is a fibrous layer comprising polyacrylate-based particles or a polyacrylate-based coating bound to the fibrous layer. A further example of a suitable material is a superabsorbent foam, for example a polyacrylate-based foam. A polyacrylate-based foam is produced by means of a solution, which at least consists of monomer, crosslinking agent, initiator and surfactant, being saturated and pressurized with carbon dioxide in a vessel under agitation. When the solution is removed from the vessel through a nozzle, the solution expands and a foamed structure is obtained. The foamed structure is then locked by initiating polymerization and cross-linking, for example by UV radiation.

A further example of a suitable material in the liquid-receiving zone 110 is a layer of continuous fibres which have been bonded to one another in a bonding pattern at points or along lines or in some regions, but otherwise are essentially non-bonded to one another. Such a material can also be used as an integrated cover sheet/liquid-receiving sheet in the liquid-receiving zone.

The difference in pore size, between the liquid-receiving zone with the first, greater mean pore size and the area which has the second, lesser mean pore size, is obtained, for example, by a difference in density between the different materials, although the desired difference in pore size can also be obtained at the same density but with different types of material.

The second sheet 106 is a liquid-storing sheet. The liquid-storing sheet is preferably a fibre structure which contains superabsorbent, i.e. polymers with the ability to absorb many times their own weight of water or body fluid. The superabsorbent is in the form of powder, flakes, fibres, granules or the like. The superabsorbent can be mixed with the fibre material or can be applied in the form of one or more layers between layers of fibre. The superabsorbent can also be a foam structure. Moreover, the second sheet 106 can also comprise a liquid-spreading layer.

The superabsorbent is, for example, particulate and is either uniformly distributed in the liquid-storing sheet or is distributed with varied concentration in the longitudinal direction and/or direction of thickness of the absorbent structure. It is also conceivable to have a substantially pure layer of superabsorbent as the storing sheet. In order not to block and prevent spread of liquid, it is possible for example to have a superabsorbent material which is also able to swell under normally occurring pressure forces. The feature which characterizes such a superabsorbent is a high degree of crosslinking which makes it more difficult to compress compared to a gel with a lower degree of crosslinking. The liquid-storing sheet can of course also be completely free of superabsorbent or can contain several different types of superabsorbents. The superabsorbent material can also be formed to give a foam.

The body fluid released, for example urine, is quickly taken up in the liquid-receiving zone and is spread out farther to the area having the second, lesser pore size and to the second sheet, i.e. the liquid-storing sheet 106. The liquid-receiving zone is drained of liquid and is then ready to accept the next dose of liquid. The liquid-storing sheet 106 has the capacity to store several doses of liquid.

Figure 2A:
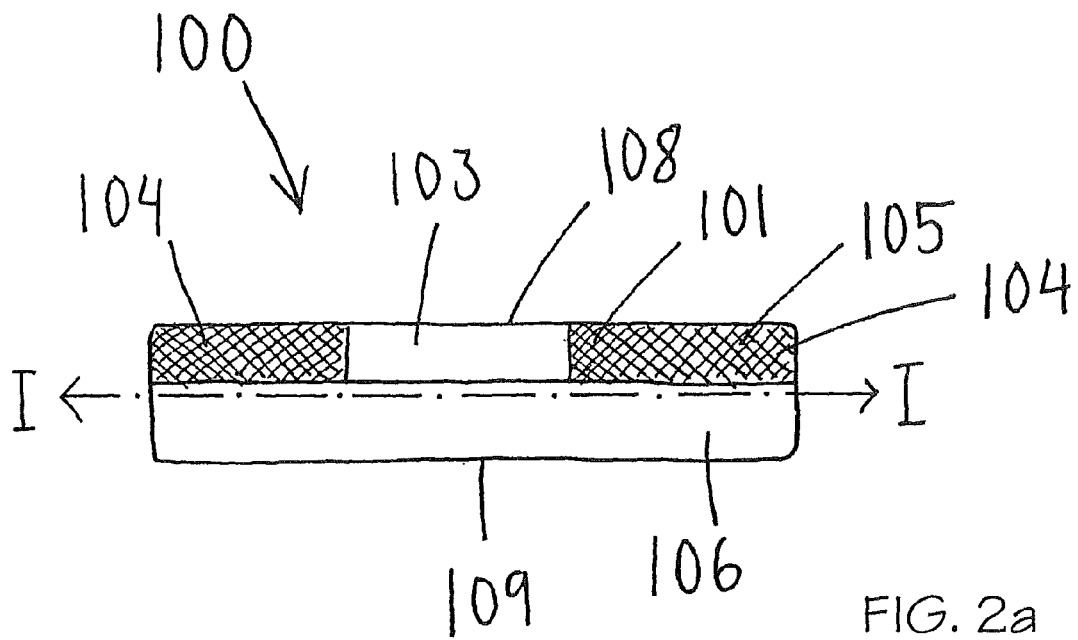
FIG. 2a shows a cross section through the absorbent structure shown in FIG. 1.

FIG. 2a shows a cross section of the absorbent structure 100 shown in FIG. 1, through the transverse centre line I, FIG. 2a thus showing the Cross section of the middle portion 101 of the absorbent structure 100. Thus, FIG. 2a shows the first sheet 105 of the absorbent structure 100, and its second sheet 106. In its plane, the absorbent structure 100 also has an upper face 108 and an opposite lower face 109. FIG. 2a moreover shows the central portion 103 of the absorbent structure and two opposite edge portions 104. In the middle portion 101 of the absorbent structure 100, the edge portions 104 of the absorbent structure thus have the first mean pore size, and the central portion 103 has the second mean pore size in the middle portion 101 of the absorbent structure. The first mean pore size is greater than the second mean pore size.

Figure 2B:
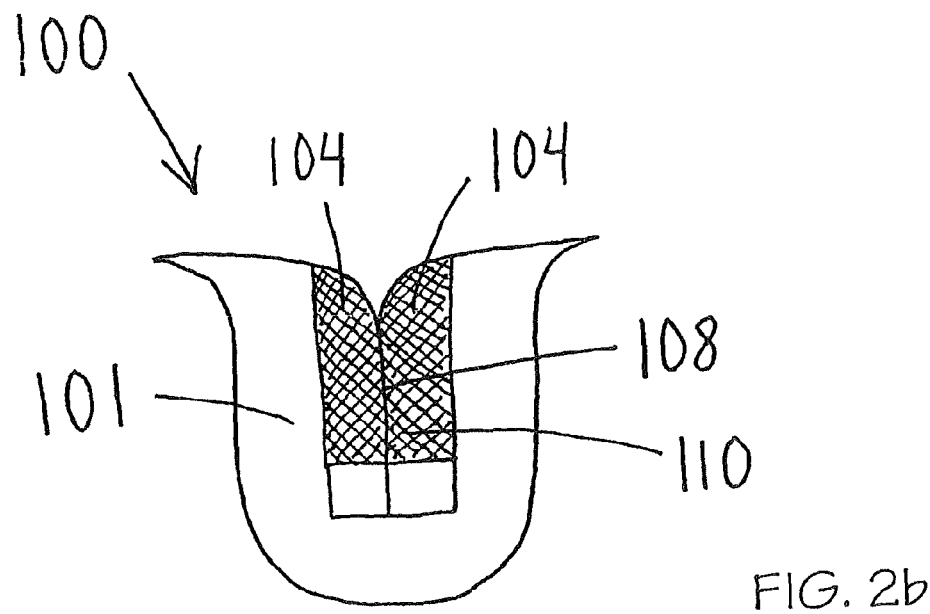
FIG. 2b shows a cross section through the absorbent structure shown in FIG. 1, where the absorbent structure is intended to be worn by a user in An absorbent article.

FIG. 2b shows a cross section of the absorbent structure shown in FIG. 1, the absorbent structure here being intended to be worn by a user in an absorbent article. When using the absorbent structure in an absorbent article, the absorbent structure, at least in the middle portion 101, is intended to be folded about its longitudinal centre line II-II. This means that at least the upper face 108 on one side of the longitudinal centre line II-II in the middle portion 101 lies against the upper face on the other, opposite side of the longitudinal centre line II-II in the middle portion 101 of the absorbent structure. This means that those portions which have the greater, first mean pore size constitute a liquid-receiving zone 110. When the absorbent article is in use, the edge portions 104 of the absorbent structure in the middle portion 101 thus constitute that part of the absorbent structure 100 which is placed in the area in the absorbent article which is first wetted, i.e. the area which constitutes the liquid-receiving zone 110. According to another alternative, an absorbent article which comprises the absorbent structure 100 is folded when the article is placed on the user. In this case, the whole article is folded along the longitudinal centre axis of the article, so that at least parts of the liquid permeable cover sheet on each side of the longitudinal centre axis are folded onto one another.

Figure 3A:
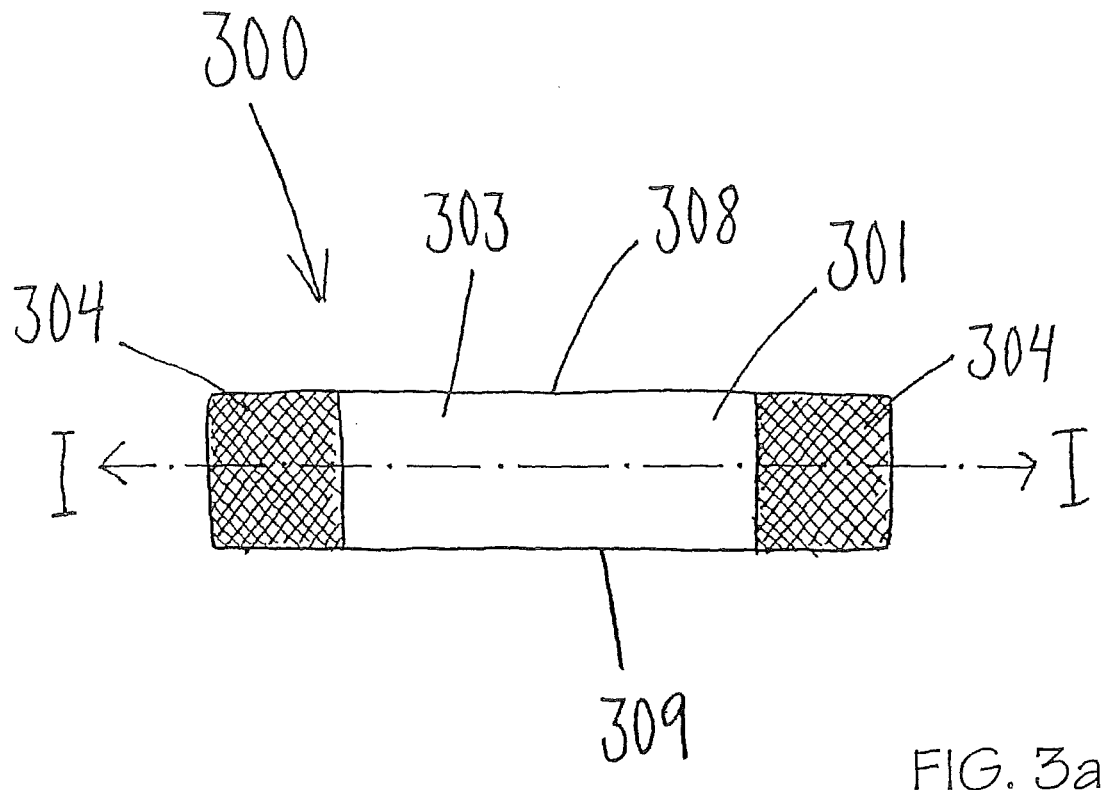
FIG. 3a shows a cross section through an alternative embodiment of an absorbent structure according to the invention.

FIG. 3a shows a cross section, on a transverse centre line I-I, through an alternative embodiment of an absorbent structure 300 according to the invention. FIG. 3a thus shows the cross section of the middle portion 301 of the absorbent structure 300. In its plane, the absorbent structure 300 has an upper face 308 and an opposite lower face 309. In its direction of thickness, the absorbent structure 300 is made up of just one sheet. In the transverse direction, the absorbent structure 300 has a central portion 303 and two edge portions 304 on each side of the central portion 303. The absorbent structure 300 has areas with different mean pore size. The edge portions 304 of the absorbent structure thus have a first mean pore size, and the central portion 303 has the second mean pore size. The first mean pore size is greater than the second mean pore size. This means that the edge portions 304 also preferably have a more open and bulkier structure than the structure in the central portion 303.

Figure 3B:
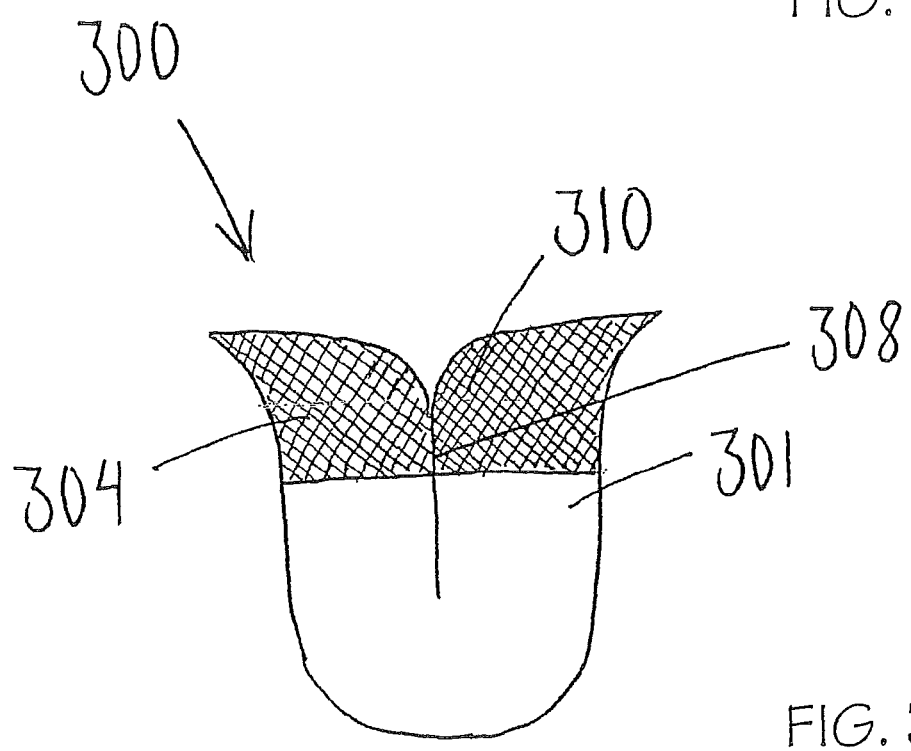
FIG. 3b shows a cross section through the absorbent structure shown in FIG. 3a, where it is intended to be worn by a user in an absorbent article.

FIG. 3b shows a cross section of the absorbent structure 300 shown in FIG. 3a, the absorbent structure here being intended to be worn by a user in an absorbent article. When using the absorbent structure 300 in an absorbent article, the absorbent structure 300, at least in the middle portion 301, is intended to be folded about its longitudinal centre line II-II. The absorbent structure 300 is intended to be folded about the longitudinal centre line such that the upper face 308 on one side of the longitudinal centre line II-II, at least in the middle portion 301, lies against the upper face 308 on the opposite side of the longitudinal centre line II-II. This means that the upper faces 308 on the edge portions 304 lie against one another and in this way the two edge portions 304 together constitute the area of the absorbent structure 300 which is first wetted, i.e. the area constituting the liquid-receiving zone 310. According to another alternative, an absorbent article which comprises the absorbent structure 300 is folded when the article is placed on the user. In this case, the whole article is folded along the longitudinal centre axis of the article, so that at least parts of the liquid permeable cover sheet on each side of the longitudinal centre axis are folded onto one another.

Figure 4:
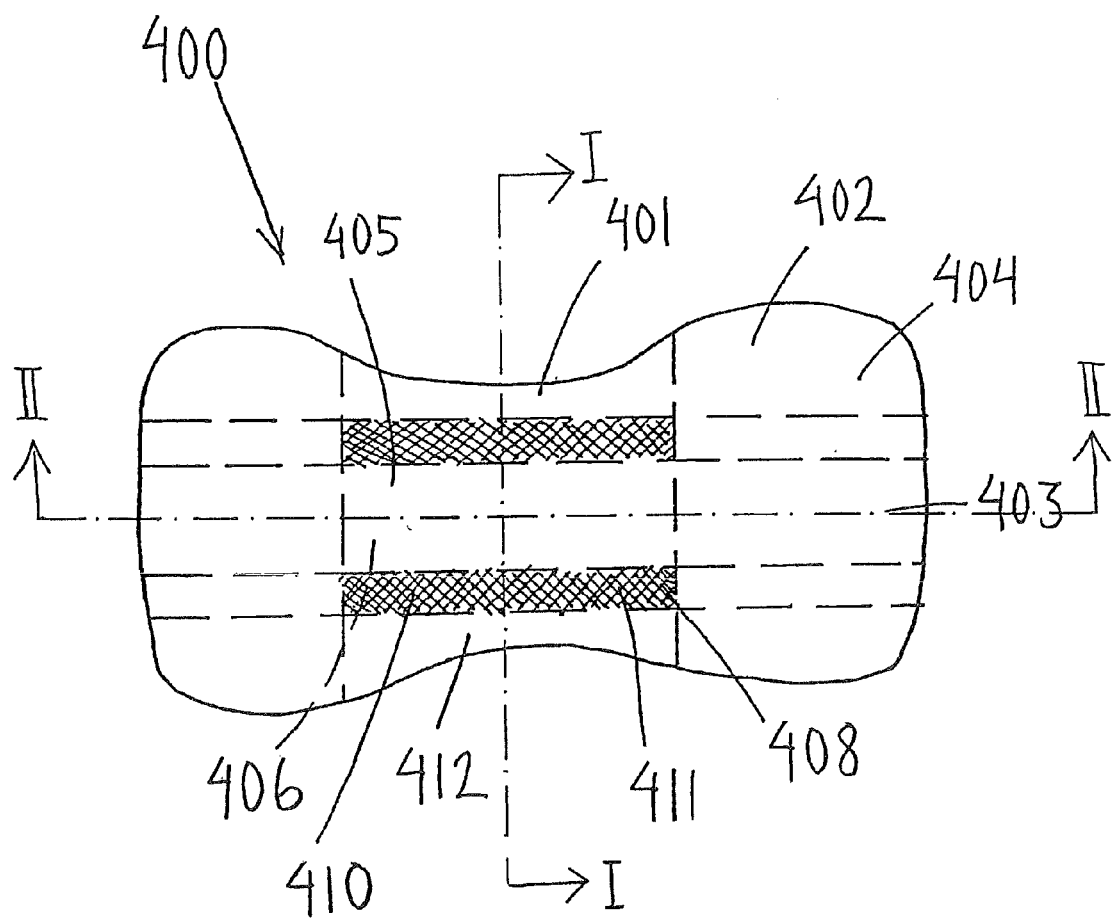
FIG. 4 shows a plan view of an alternative embodiment of an absorbent structure according to the invention.

FIG. 4 shows an alternative preferred embodiment of an absorbent structure according to the present invention. The absorbent structure 400 shown in FIG. 4 has, in its plane, a transverse direction which is shown by a transverse centre line I-I, and a longitudinal direction which is shown by a longitudinal centre line II-II. In the longitudinal direction, the absorbent structure 400 has a middle portion 401, and two opposite end portions 402. In the transverse direction, the absorbent structure 400 has a central portion 403 and two edge portions 404 on opposite sides of the central portion 403. In the direction of thickness, the absorbent structure 400 further comprises a first sheet 405 and a second sheet 406. The first sheet 405 is the sheet of the absorbent structure which, during use in an absorbent article, is intended to be nearest to the user. The first sheet 405 has areas with different mean pore sizes. In the middle portion 401 of the absorbent structure 400, the edge portions 404 of the absorbent structure have a first mean pore size and the central portion 403 has a second mean pore size. The edge portions 404 of the absorbent structure are moreover divided into an inner edge portion 411 and an outer edge portion 412. The inner edge portion 411 is the portion which is situated nearest to the central portion 403, and the outer edge portion 412 is the portion which is situated farthest away from the central portion 403. In the middle portion 401 of the absorbent structure, the inner edge portion 411 and the outer edge portion 412 have a different mean pore size. In the absorbent structure 400, the outer edge portion 412 has the same mean pore size as the central portion 403. The first mean pore size, i.e. the mean pore size in the edge portion 404 in the middle portion 401, is thus the mean pore size calculated on both the portion constituting the inner edge portion 411 and the portion constituting the outer edge portion 412 in the middle portion 401 of the absorbent structure 400.

The two end portions 402 of the first sheet 405 also have the second mean pore size. The first mean pore size is greater than the second mean pore size. When the absorbent structure is used in an absorbent article, the absorbent structure 400 is intended to be folded on the longitudinal centre line II-II such that the upper face 408 on one side of the longitudinal centre line II-II in the inner edge portion 411 of the middle portion 401 lies against the upper face on the other, opposite side of the longitudinal centre line II-II in the inner edge portion 411 of the middle portion 401, and the portions which have the greater, first mean pore size constitute a liquid-receiving zone 410. During use of the absorbent article, the inner edge portions 411 of the absorbent structure in the middle portion 401 define the part of the absorbent structure that is placed in the area in the absorbent structure 400 which is first wetted, namely the liquid-receiving zone 410. According to another alternative, an absorbent article which comprises the absorbent structure 400 is folded when it is placed on the user. In this case, the whole article is folded along the longitudinal centre axis of the article, so that at least parts of the liquid permeable cover sheet on each side of the longitudinal centre axis are folded onto one another.

Figure 5:
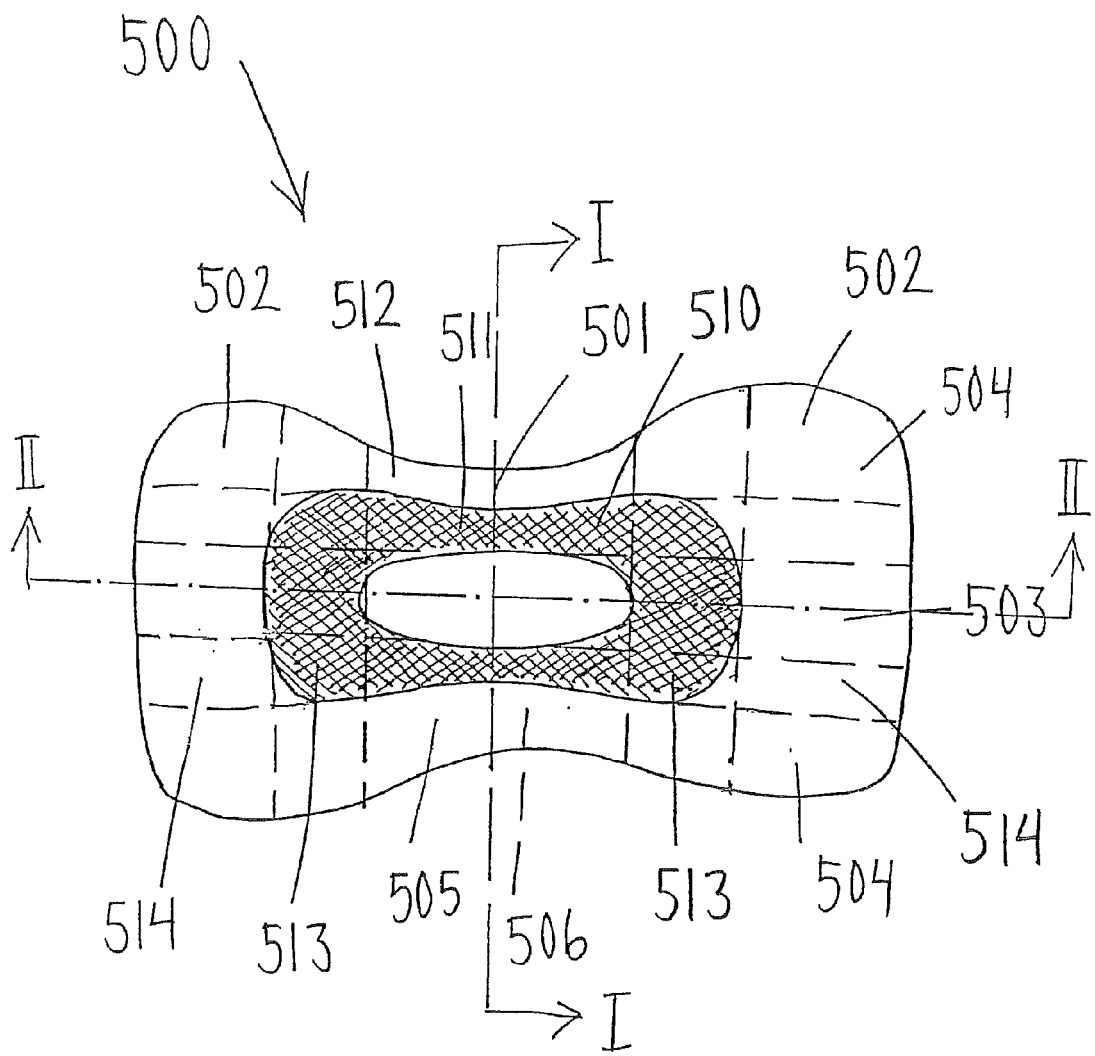
FIG. 5 shows a plan view of a further alternative embodiment of an absorbent structure according to the invention.

FIG. 5 shows an alternative preferred embodiment of an absorbent structure according to the invention. The absorbent structure 500 has, in its plane, a transverse direction which is shown by a transverse centre line I-I, and a longitudinal direction which is shown by a longitudinal centre line II-II. In the longitudinal direction, the absorbent structure 500 has a middle portion 501, and two opposite end portions 502. In the transverse direction, the absorbent structure 500 has a central portion 503 and two edge portions 504 on opposite sides of the central portion 503. In the direction of thickness, the absorbent structure 500 further comprises a first sheet 505 and a second sheet 506. The first sheet 505 is the sheet of the absorbent structure which, during use in an absorbent article, is intended to be nearest to the user. The first sheet 505 has areas with different mean pore sizes. In the middle portion 501 of the absorbent structure 500, the edge portions 504 of the absorbent structure have a first mean pore size and the central portion 503 has a second mean pore size. The edge portions 504 of the absorbent structure are divided into an inner edge portion 511 and an outer edge portion 512. The inner edge portion 511 is the portion which is situated nearest to the central portion 503, and the outer edge portion 512 is the portion which is situated farthest away from the central portion 503. In the middle portion 501 of the absorbent structure, the inner edge portion 511 and the outer edge portion 512 have a different mean pore size. In the absorbent structure 500, the outer edge portion 512 has the same mean pore size as the central portion 503 in the middle portion 501. The first mean pore size, i.e. the mean pore size in the edge portion 504 in the middle portion 501, is thus the mean pore size calculated on both the portion constituting the inner edge portion 511 and the portion constituting the outer edge portion 512 in the middle portion 501 of the absorbent structure.

The two end portions 502 of the first sheet 505 in FIG. 5 are also divided into an inner end portion 513 and an outer end portion 514. The inner end portion 513 is situated nearest to the middle portion 501, and the outer end portion 514 is situated farthest away from the middle portion 501. The inner end portion has two different portions of different mean pore size. In the inner end portion 513, the central portion 503 and the inner edge portion 511 have a greater mean pore size than the outer edge portion 512.

When the absorbent structure is used in an absorbent article, the absorbent structure is intended to be folded on its longitudinal centre axis II-II such that the upper face 508 on one side of the longitudinal centre line II-II in the inner edge portion 511 of the middle portion 501 lies against the upper face on the other, opposite side of the longitudinal centre axis II-II in the inner edge portion 511 of the middle portion 501, and the portions which have the greater, first mean pore size constitute a liquid-receiving zone 510. During use of the absorbent article, the inner edge portions 511 of the absorbent structure in the middle portion 501 constitute the part of the absorbent structure that is placed in the area in the absorbent structure which is first wetted, namely the liquid-receiving zone 510. According to another alternative, an absorbent article which comprises the absorbent structure 500 is folded when it is placed on the user. In this case, the whole article is folded along the longitudinal centre axis II-II of the article, so that at least parts of the liquid permeable cover sheet on each side of the longitudinal centre axis II are folded onto one another.

Figure 6:
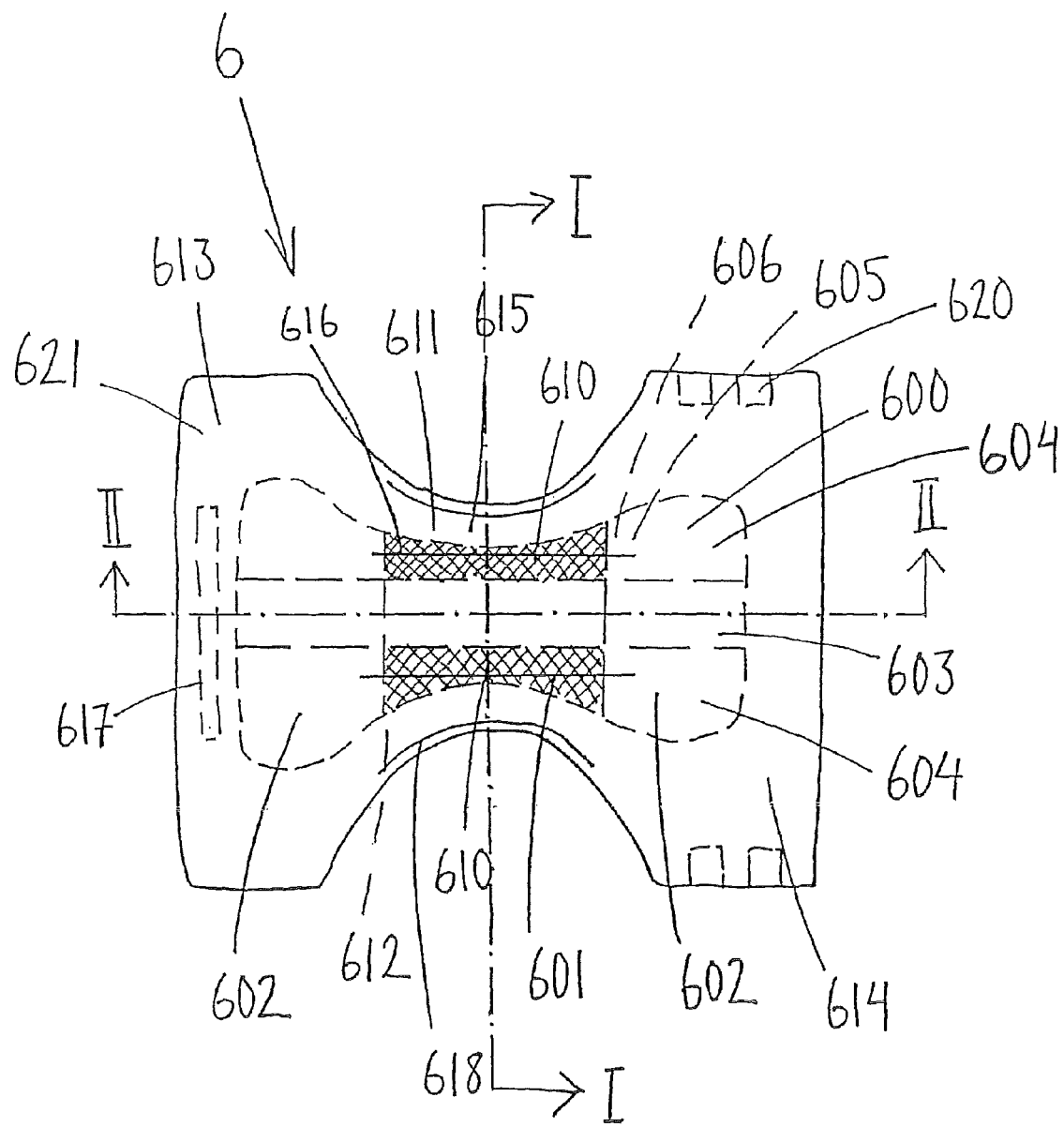
FIG. 6 shows an incontinence protector comprising an absorbent structure according to the invention.

FIG. 6 shows an incontinence protector 6 in the stretched-out state and viewed from the direction of the face which, during use, is intended to lie nearest the user. The incontinence protector 6 comprises an absorbent structure 600 according to a further preferred embodiment of the present invention. In the longitudinal direction, the absorbent structure 600 thus has a middle portion 601, and two opposite end portions 602. In the transverse direction, the absorbent structure 600 has a central portion 603 and two edge portions 604 on opposite sides of the central portion 603. In its direction of thickness, the absorbent structure 600 further comprises a first sheet 605 and a second sheet 606. The first sheet 605 is the sheet of the absorbent structure which, during use of an absorbent article with the absorbent structure, is intended to be nearest to the user. The first sheet 605 has areas with different mean pore sizes. In the edge portions 604 of the middle portion 601, the first sheet has a first mean pore size and, in the central portion 603 it has a second mean pore size. The two end portions 602 of the first sheet 605 also have the second mean pore size. The first mean pore size is greater than the second mean pore size. When the absorbent structure is used in an absorbent article, the absorbent structure 600 is intended to be folded on the longitudinal centre line II-II such that at least the upper face 608 on one side of the longitudinal centre line II-II in the middle portion 601 lies against the upper face on the other side of the longitudinal centre line II-II in the middle portion 601 of the absorbent structure, and the portions which have the greater, first mean pore size constitute a liquid-receiving zone 610. In a preferred embodiment, the liquid-receiving zone 610 has a density of between 0.02 and 0.2 g/cm3, preferably between 0.06 and 0.15 g/cm3, and the area having the second, lesser mean pore size has a density of between 0.1 and 1.0 g/cm3, preferably between 0.12 and 0.6 g/cm3. According to another alternative, the incontinence protector 6 is folded when it is placed on the user. In this case, the incontinence protector 6 is folded along its longitudinal centre axis II-II, so that at least parts of the liquid-permeable cover sheet 611 on each side of the longitudinal centre axis II-II are folded onto one another. During use of the absorbent article, the edge portions 604 of the absorbent structure in the middle portion 601 constitute the part of the absorbent structure that is placed in the area in the absorbent structure 600 which is first wetted, i.e. the liquid-receiving zone 610.

The incontinence protector shown in FIG. 6 further comprises a liguid-permeable cover sheet 611 and a backing sheet 612, the absorbent structure 600 being enclosed between the two cover sheets 611, 612. The liquid-permeable cover sheet 611 includes, for example, a nonwoven material, perforated plastic film or a laminate thereof. Another example of a material for the liquid-permeable cover sheet 611 is a sheet of continuous fibres which have been bonded at points, along lines or in some regions in a bonding pattern but are otherwise not bonded to one another. The backing sheet 612 can include a plastic sheet, a nonwoven sheet or a laminate thereof. The backing sheet is, for example, of the breathable type.

The incontinence protector 6 is intended to surround the lower part of the user's trunk in the manner of a pair of absorbent pants. The incontinence protector 6 has a front end portion 613 intended to be directed forwards on the user during use of the incontinence protector, and a rear end portion 614 intended to be directed rearwards on the user during use, and a narrower crotch portion 615 which is located between the front end portion 613 and the rear end portion 614 and is intended to be arranged between the user's legs.

The incontinence protector 6 moreover has elastic members. These elastic members in the incontinence protector 6 constitute raised elastic liquid barriers 616, waist elastic 617 and leg elastic 618.

The elastic raised liquid barriers 616 are fixed to the liquid-permeable cover sheet 611 and are designed to prevent leakage of liquid. The elastic raised liquid barriers are made of a liquid-tight material, for example a hydrophobic nonwoven sheet, and comprise one or more elastic threads, which elastic threads ensure that the liquid barriers have elasticity and, during use, are raised from the liquid-permeable cover sheet 611.

The waist elastic 617 in the incontinence protector 6 is preferably made of an elastic tape material and is placed slightly in from the front end edge of the article.

The leg elastic 618 of the incontinence protector 6 preferably include elongate elastic members, such as one or more elastic threads or an elastic tape element. The elongate elastic members are placed along the longitudinal edges of the article, at least along the crotch portion of the article, and constitute leg bands. The elastic threads or elastic tapes are pretensioned, i.e. stretched to a certain extent before the elastic threads or tapes are anchored to the liquid-permeable cover sheet 611. In this way, the elastic threads are drawn together and the material to the inside of the elastic threads is pleated slightly so as to give a tighter fit around the user's legs during use of the incontinence protector.

To allow the incontinence protector 6 to be fastened together to give the desired pants shape, the incontinence protector 6 comprises a fastening arrangement for joining the incontinence protector together to give a pants shape. The fastening arrangement comprises a first member 620 and a second member 621. In the incontinence protector 6 shown in FIG. 6, tape flaps arranged near the rear end edge of the incontinence protector constitute the first member 620, and the outside of the front end portion of the incontinence protector constitutes the second member 621 of the fastening arrangement. Thus, during use, the tape flaps are secured to the outside of the front end portion of the incontinence protector, near the transverse front end edge of the article, and the incontinence protector 6 is held together around the user's waist. Other fastening members such as VELCRO closures, hooks or the like are of course conceivable.

Figure 8:
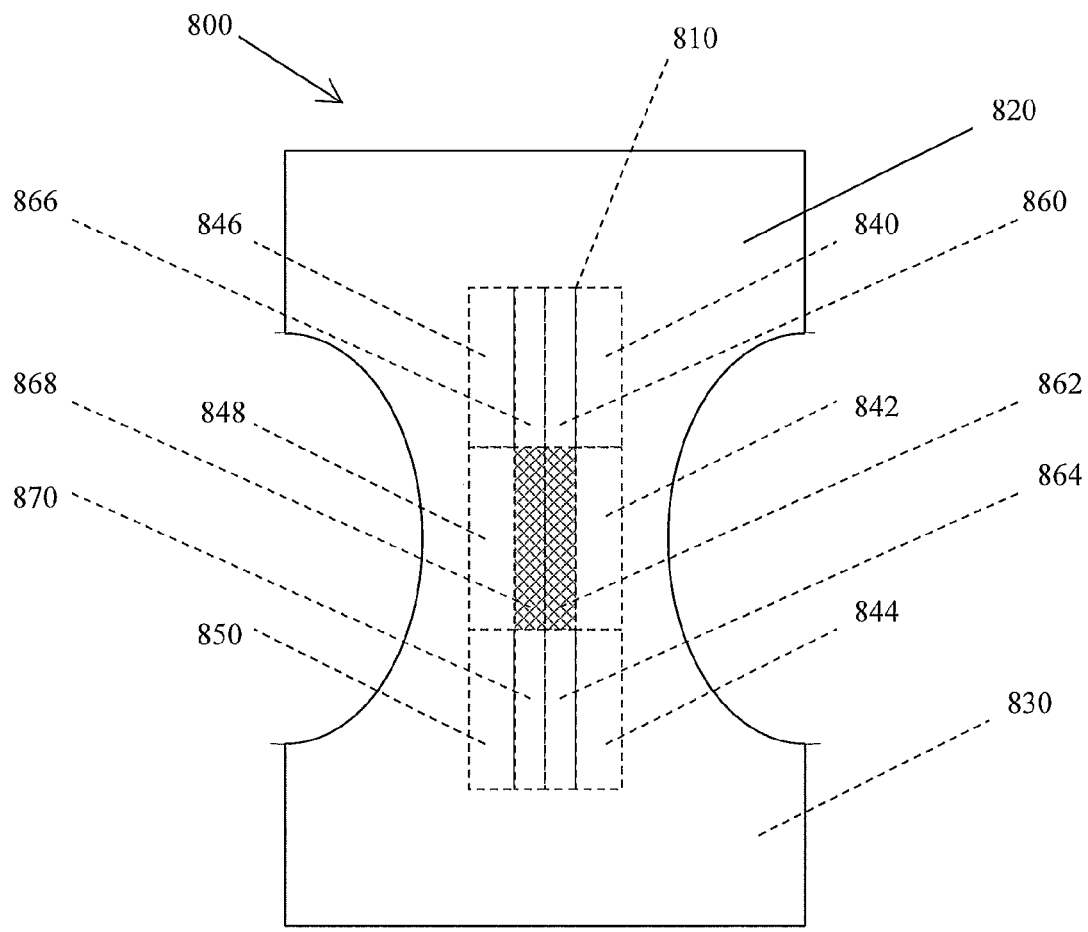
FIG. 8 shows an embodiment of a folded absorbent structure between a cover sheet and a backing sheet.

FIG. 8 shows an incontinence protector 800 in a stretched-out state and viewed from the direction of the face which, during use, is intended to lie nearest the user. The incontinence protector 800 comprises an absorbent structure 810 according to an embodiment of the invention, as shown in FIGS. 2a and 2b. The incontinence protector shown in FIG. 8 further comprises a liquid-permeable cover sheet 820 and a backing sheet 830, the absorbent structure 810 being enclosed between the two cover sheets 820, 830. In the longitudinal direction, the absorbent structure 810 thus has a middle portion, and two opposite end portions. In the transverse direction, the absorbent structure 810 has a central portion and two edge portions on opposite sides of the central portion. In its direction of thickness, the absorbent structure 810 further comprises a first sheet and a second sheet. The first sheet is the sheet of the absorbent structure 810 which, during use of the incontinence protector 800, is intended to be nearest to the user. The first sheet has areas with different mean pore sizes. The absorbent structure is folded along a longitudinal centre line such that at least an upper face on one side of the longitudinal centre line lies against an upper face on the other side of the longitudinal centre line. In the folded state, the edge portions 840, 846, 860, 866, 842, 848, 862, 868, 864, 870, 844, 850 of the absorbent structure face towards the liquid-permeable cover sheet 820. Edge portion 868 is formed from the middle portion of a first edge portion of the first sheet. Edge portion 862 is formed from the middle portion of a second edge portion of the first sheet. Edge portion 848 is formed from the middle portion of a first edge portion of the second sheet. Edge portion 842 is formed from the middle portion of a second edge portion of the second sheet. Edge portion 866 is formed from a first end portion of a first edge portion of the first sheet. Edge portion 860 is formed from a first end portion of a second edge portion of the first sheet. Edge portion 846 is formed from a first end portion of a first edge portion of the second sheet. Edge portion 840 is formed from a first end portion of a second edge portion of the second sheet. Edge portion 870 is formed from a second end portion of a first edge portion of the first sheet. Edge portion 864 is formed from a second end portion of a second edge portion of the first sheet. Edge portion 850 is formed from a second end portion of a first edge portion of the second sheet. Edge portion 844 is formed from and a second end portion of a second edge portion of the second sheet.

We claim:

1. An absorbent article having a transverse direction, a longitudinal direction, a longitudinal centre axis extending in the longitudinal direction, and a direction of thickness, the article comprising:
    a liquid-permeable cover sheet arranged on an upper surface of the article,
    a backing sheet arranged on a lower surface of the article, and
    a folded absorbent structure enclosed between the liquid-permeable cover sheet and the backing sheet, having a transverse direction, a longitudinal direction, a longitudinal centre axis extending in the longitudinal direction, and a direction of thickness,
    the absorbent structure comprising a sheet, wherein at the time the absorbent structure is folded:
    the sheet is of uniform thickness, and defines, in the longitudinal direction, a middle portion and two opposite end portions and, in the transverse direction, a central portion and two opposite edge portions, and the edge portions in the middle portion of the sheet have a first mean pore size throughout the entire uniform thickness of the sheet and the central portion in the middle portion of the sheet has a second mean pore size throughout the entire uniform thickness of the sheet, the first mean pore size being greater than the second mean pore size,
    the absorbent structure being folded transversely in half along the longitudinal centre axis of the absorbent structure along the entire absorbent structure along the middle portion of the sheet,
    wherein an upper face of the edge portion in the middle portion of the sheet on one side of the longitudinal centre axis of the absorbent structure prior to folding and a corresponding upper face of the edge portion in the middle portion of the sheet on the other side of the longitudinal centre axis of the absorbent structure prior to folding are brought together when the absorbent structure is folded transversely in half to lie against one another at a plane of the longitudinal centre axis on an upper surface of the folded absorbent structure such that the edge portions of the sheet having the greater, first mean pore size form an area of the folded absorbent structure that during use receives liquid first before other areas of the folded absorbent structure and thus constitutes a liquid-receiving zone, the other areas of the folded absorbent structure including the central portion in the middle portion of the sheet having the lesser, second mean pore size which underlies the edge portions in the direction of thickness of the folded absorbent structure.

2. The absorbent article according to claim 1,
wherein the edge portions in the middle portion of the sheet have the first mean pore size throughout the entire direction of thickness of the absorbent structure, and
wherein the central portion in the middle portion of the sheet has the second mean pore size throughout the entire uniform thickness of the absorbent structure.

3. The absorbent article according to claim 2, wherein the edge portions of the end portions in the sheet also have the first mean pore size within at least part of the uniform thickness of the absorbent structure.

4. The absorbent article according to claim 1, wherein the absorbent structure, in the direction of thickness, has a first sheet and a second sheet, the first sheet having a smaller extent in the longitudinal direction than the second sheet.

5. The absorbent article according to claim 1, wherein the first mean pore size is at least 1.1 times as great as the second mean pore size.

6. The absorbent article according to claim 1, wherein the liquid-receiving zone has a density of between 0.02 and 0.2 g/cm$^3$, and the area having the second, lesser mean pore size has a density of between 0.1 and 1.0 g/cm$^3$.

7. Absorbent article according to claim 6, wherein the liquid-receiving zone has a density of between 0.06 and 0.15 g/cm$^3$.

8. The absorbent article according to claim 6, wherein the area having the second, lesser mean pore size has a density of between 0.12 and 0.6 g/cm$^3$.

9. The absorbent article of claim 1, wherein said absorbent article is selected from the group consisting of a diaper, an incontinence protector, and a sanitary towel.

10. The absorbent article of claim 1, wherein the fold along the central axis is the only fold of the absorbent structure.

11. The absorbent article of claim 1, wherein the absorbent structure, at the time it is folded to form the folded absorbent structure, is of uniform thickness.

12. The absorbent article of claim 1, wherein the liquid permeable cover sheet is folded with the absorbent structure such that an upper face of a first portion of the cover sheet disposed over the edge portion in the middle portion of the sheet on one side of the longitudinal centre axis of the absorbent structure prior to folding and a corresponding upper face of a second portion of the cover sheet disposed over the edge portion in the middle portion of the sheet on the other side of the longitudinal centre axis of the absorbent structure prior to folding are brought together when the absorbent structure is folded transversely in half; to lie against one another at a plane of the longitudinal centre axis of the absorbent structure on an upper surface of the absorbent structure and thus also constitute the liquid receiving zone.

13. The absorbent article of claim 12, wherein the portions of the cover sheet brought together are directly attached to each other is directly attached to the second portion of the cover sheet.

14. The absorbent article of claim 13, wherein the direct attachment is by adhesive bonding or thermal welding.

15. The absorbent article of claim 1, wherein the upper faces of the edge portions in the middle portion of the sheet brought together are directly attached to each other.

16. The absorbent article of claim 15, wherein the direct attachment is by adhesive bonding or thermal welding.

17. A folded absorbent structure having a transverse direction, a longitudinal direction, a longitudinal centre axis extending in the longitudinal direction, and a direction of thickness, the absorbent structure comprising:
a sheet, wherein at the time the absorbent structure is folded:
the sheet is of uniform thickness, and defines, in the longitudinal direction, a middle portion and two opposite end portions and, in the transverse direction, a central portion and two opposite edge portions, and the edge portions in the middle portion of the sheet have a first mean pore size throughout the entire uniform thickness of the sheet and the central portion in the middle portion of the sheet has a second mean pore size throughout the entire uniform thickness of the sheet, the first mean pore size being greater than the second mean pore size,
the absorbent structure being folded transversely in half along the longitudinal centre axis of the absorbent structure along the entire absorbent structure along the middle portion of the sheet,
wherein an upper face of the edge portion in the middle portion of the sheet on one side of the longitudinal centre axis of the absorbent structure prior to folding and a corresponding upper face of the edge portion in the middle portion of the sheet on the other side of the longitudinal centre axis of the absorbent structure prior to folding are brought together when the absorbent structure is folded transversely in half to lie against one another at a plane of the longitudinal centre axis on an upper surface of the folded absorbent structure such that the edge portions of the sheet having the greater, first mean pore size form an area of the folded absorbent structure that during use receives liquid first before other areas of the folded absorbent structure and thus constitutes a liquid-receiving zone, the other areas of the folded absorbent structure including the central portion in the middle portion of the sheet having the lesser, second mean pore size which underlies the edge portions in the direction of thickness of the folded absorbent structure.

* * * * *